(12) United States Patent
Wu et al.

(10) Patent No.: US 12,178,407 B2
(45) Date of Patent: Dec. 31, 2024

(54) IMAGE SENSOR PACKAGE AND MINIATURIZED ENDOSCOPE HAVING A SCATTERING LAYER TO PROVIDE UNIFORM ILLUMINATION

(71) Applicant: Medimaging Integrated Solution, Inc., Hsinchu (TW)

(72) Inventors: Shangyi Wu, Hsinchu (TW); Jiunwei Chen, Hsinchu (TW); Jia-De Zhou, Hsinchu (TW); Tseng Shen Tseng, Hsinchu (TW)

(73) Assignee: MEDIMAGING INTEGRATED SOLUTION, INC., Hsinchu (TW)

( * ) Notice: Subject to any disclaimer, the term of this patent is extended or adjusted under 35 U.S.C. 154(b) by 40 days.

(21) Appl. No.: 17/957,251

(22) Filed: Sep. 30, 2022

(65) Prior Publication Data

US 2023/0108867 A1 Apr. 6, 2023

(30) Foreign Application Priority Data

Oct. 4, 2021 (TW) ................................. 110136950

(51) Int. Cl.
*A61B 1/05* (2006.01)
*A61B 1/00* (2006.01)
(Continued)

(52) U.S. Cl.
CPC .......... *A61B 1/051* (2013.01); *A61B 1/00114* (2013.01); *A61B 1/00124* (2013.01); *A61B 1/0607* (2013.01); *A61B 1/0676* (2013.01); *A61B 1/07* (2013.01); *H01L 31/02005* (2013.01); *H01L 31/0203* (2013.01);
(Continued)

(58) Field of Classification Search
CPC . A61B 1/051; A61B 1/00114; A61B 1/00124; A61B 1/0607; A61B 1/0676; A61B 1/07; A61B 1/00009; A61B 1/00096; A61B 1/0011; A61B 1/0684; H01L 31/02005; H01L 31/0203; H01L 31/02164;
(Continued)

(56) References Cited

U.S. PATENT DOCUMENTS

| | | | |
|---|---|---|---|
| 11,309,299 B2* | 4/2022 | Wu | ................... H05K 1/189 |
| 2010/0010138 A1* | 1/2010 | Kikuchi | ................ G02B 1/04 |
| | | | 524/1 |

(Continued)

*Primary Examiner* — Pritham D Prabhakher
(74) *Attorney, Agent, or Firm* — Muncy, Geissler, Olds & Lowe, P.C.

(57) ABSTRACT

An image sensor package includes a substrate, an image sensor, a plurality of light-emitting elements, and a scattering layer. The substrate includes a plurality of first conductive contacts, a plurality of second conductive contacts, and a plurality of third conductive contacts, wherein the second conductive contacts and the third conductive contacts are electrically connected with the corresponding first conductive contacts. The image sensor is disposed on the substrate and electrically connected to the second conductive contacts. The light-emitting elements are disposed on the substrate and electrically connected with the third conductive contacts. The scattering layer covers at least one sidewall of the light-emitting elements. The abovementioned image sensor package can provide better illumination effects. An endoscope including the abovementioned image sensor package is also disclosed.

28 Claims, 8 Drawing Sheets

(51) Int. Cl.
*A61B 1/06* (2006.01)
*A61B 1/07* (2006.01)
*H01L 31/02* (2006.01)
*H01L 31/0203* (2014.01)
*H01L 31/0216* (2014.01)
*H01L 31/0232* (2014.01)
*H01L 31/173* (2006.01)

(52) U.S. Cl.
CPC .. *H01L 31/02164* (2013.01); *H01L 31/02325* (2013.01); *H01L 31/173* (2013.01); *A61B 1/00009* (2013.01)

(58) Field of Classification Search
CPC .. H01L 31/02325; H01L 31/173; H01L 31/16
USPC ......................................................... 348/272
See application file for complete search history.

(56) References Cited

U.S. PATENT DOCUMENTS

| | | | |
|---|---|---|---|
| 2010/0056864 A1* | 3/2010 | Lee .................. | A61B 1/041 |
| | | | 600/109 |
| 2012/0031977 A1* | 2/2012 | Havens ............. | H01L 27/14618 |
| | | | 235/472.01 |
| 2015/0346586 A1* | 12/2015 | Lin .................... | A61B 1/0011 |
| | | | 348/68 |
| 2019/0013444 A1* | 1/2019 | Morimoto ........... | A61B 1/0653 |
| 2020/0120782 A1* | 4/2020 | Nakao ................ | A61B 1/00071 |
| 2021/0037169 A1* | 2/2021 | Numasawa ............ | A61B 1/06 |
| 2022/0072328 A1* | 3/2022 | Steier ................. | A61B 1/0646 |

\* cited by examiner

IMAGE SENSOR PACKAGE AND MINIATURIZED ENDOSCOPE HAVING A SCATTERING LAYER TO PROVIDE UNIFORM ILLUMINATION

BACKGROUND OF THE INVENTION

1. Field of the Invention

The present invention relates to an image sensor package and an endoscope, particularly to an image sensor package having enhancing illumination effect and an endoscope using the same.

2. Description of the Prior Art

An endoscope can reach cavities, which the naked eyes are unlikely to observe directly. Therefore, endoscopes have been extensively used in industry and medicine. Especially, the application of endoscopes to medicine favors medical diagnosis very much. An endoscope may access cavities of a human body through tiny channels of the human body. For an example, an endoscope may reach the lung through a bronchial tube. For another example, an endoscope may enter the bladder through the urinary tract. Hence, miniaturizing an endoscope has become an important subject of the concerned field.

Refer to FIG. 1. In a conventional endoscope 10, an image sensor 11 and light-emitting elements 12 are disposed on a flexible circuit board 13; cables 14 are soldered to the corresponding electric-conduction contacts 131 of the flexible circuit board 13. After the flexible circuit board 13 is bent to have the desired shape, the abovementioned elements are encapsulated with a plastic material to assume a fixed form in an injection-molding method. The conventional technology is more complicated in the structure and fabrication process. Further, the endoscope 10 has a larger size. Besides, the light-output surfaces of the light-emitting elements 11 are unlikely to face upwards, and the light-emitting elements 12 is hard to be disposed around the image sensor 11. Therefore, the conventional endoscope has disadvantages of low light utilization efficiency, non-uniform illumination, and likeliness of shadows and blind spots.

Accordingly, the manufacturers are eager to develop an endoscope that is miniaturized and able to provide uniform illumination.

SUMMARY OF THE INVENTION

The present invention provides an image sensor package and an endoscope using the same, wherein a scattering layer surrounds the light-emitting elements, whereby the illumination light generated by the light-emitting elements is partially stopped by the scattering layer to achieve a better illumination effect.

In one embodiment, the image sensor package of the present invention comprises a substrate, an image sensor, a plurality of light-emitting elements, and a scattering layer. The substrate includes a plurality of first conductive contacts, a plurality of second conductive contacts, and a plurality of third conductive contacts, wherein the plurality of second conductive contacts and the plurality of third conductive contacts are electrically connected with the plurality of corresponding first conductive contacts. The image sensor is disposed on the substrate and electrically connected with the plurality of second conductive contacts. The light-emitting elements are disposed on the substrate and electrically connected with the plurality of third conductive contacts and adjacent to the image sensor. The scattering layer covers at least one sidewall of the light-emitting elements.

In one embodiment, the endoscope of the present invention comprises a tube, an image sensor package, a plurality of cables, and an electric connector. The tube includes a first opening and a second opening. The end of the first opening of the tube is extended to a cavity. The image sensor package is disposed at the end of the first opening of the tube to capture images of a cavity and generate corresponding signals. The image sensor package comprises a substrate, an image sensor, a plurality of light-emitting elements, and a scattering layer. The substrate includes a plurality of first conductive contacts, a plurality of second conductive contacts, and a plurality of third conductive contacts, wherein the plurality of second conductive contacts and the plurality of third conductive contacts are electrically connected with the plurality of corresponding first conductive contacts. The image sensor is disposed on the substrate and electrically connected with the plurality of second conductive contacts. The light-emitting elements are disposed on the substrate and electrically connected with the plurality of third conductive contacts and adjacent to the image sensor. The scattering layer covers at least one sidewall of the light-emitting elements. The plurality of cables is disposed inside the tube. The electric connector is electrically connected with another end of the plurality of cables, whereby the endoscope can be electrically connected with an external electronic device in a pluggable way.

The objective, technologies, features and advantages of the present invention will become apparent from the following description in conjunction with the accompanying drawings wherein certain embodiments of the present invention are set forth by way of illustration and example.

BRIEF DESCRIPTION OF THE DRAWINGS

The foregoing conceptions and their accompanying advantages of this invention will become more readily appreciated after being better understood by referring to the following detailed description, in conjunction with the accompanying drawings, wherein.

DESCRIPTION OF THE PREFERRED EMBODIMENTS

Various embodiments of the present invention will be described in detail below and illustrated in conjunction with the accompanying drawings. In addition to these detailed descriptions, the present invention can be widely implemented in other embodiments, and apparent alternations, modifications and equivalent changes of any mentioned embodiments are all included within the scope of the present invention and based on the scope of the Claims. In the descriptions of the specification, in order to make readers have a more complete understanding about the present invention, many specific details are provided; however, the present invention may be implemented without parts of or all the specific details. In addition, the well-known steps or elements are not described in detail, in order to avoid unnecessary limitations to the present invention. Same or similar elements in Figures will be indicated by same or similar reference numbers. It is noted that the Figures are schematic and may not represent the actual size or number of the elements. For clearness of the Figures, some details may not be fully depicted.

Figure 1:
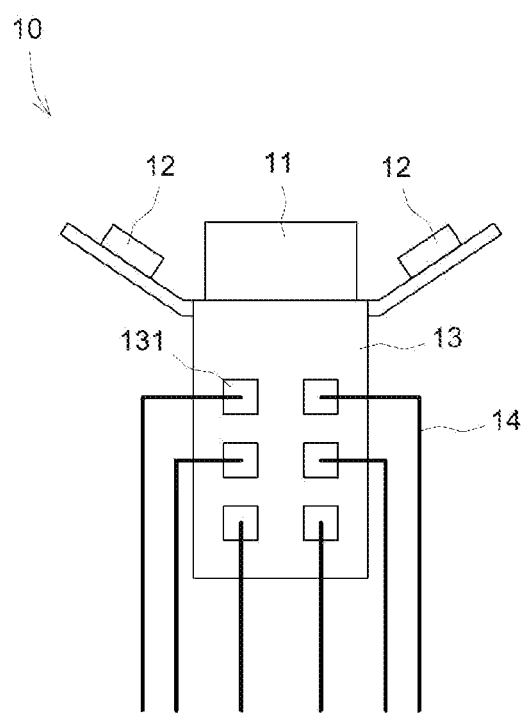
FIG. 1 is a diagram schematically showing the structure of a conventional endoscope.
Figure 2:
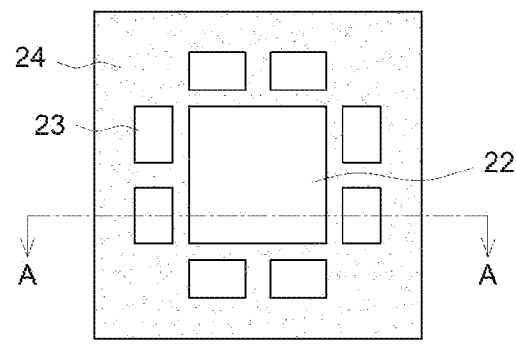
FIG. 2 is a diagram schematically showing an image sensor package according to a first embodiment of the present invention.
Figure 3:
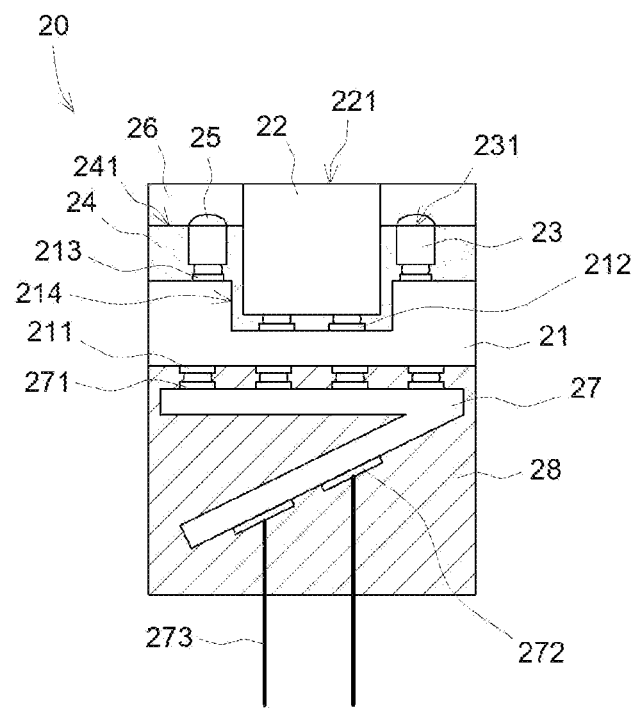
FIG. 3 is a sectional view taken along Line AA of FIG. 2 to schematically show the image sensor package according to the first embodiment of the present invention.

Refer to FIG. 2 and FIG. 3. In one embodiment, the image sensor package 20 of the present invention comprises a substrate 21, an image sensor 22, a plurality of light-emitting elements 23, and a scattering layer 24. The substrate 21 includes a plurality of first conductive contacts 211, a plurality of second conductive contacts 212, and a plurality of third conductive contacts 213, wherein the plurality of second conductive contacts 212 and the plurality of third conductive contacts 213 are electrically connected with the plurality of corresponding first conductive contacts 211 through metal routes of the substrate 21 or other appropriate electric-conduction paths. In one embodiment, the plurality of second conductive contacts 212 and the plurality of third conductive contacts 213 are disposed on one side of the substrate 21, which is opposite to the plurality of first conductive contacts 211. In one embodiment, the substrate 21 is a ceramic substrate or a substrate made of an appropriate material.

The image sensor 22 is disposed on the substrate 21 and electrically connected with the plurality of second conductive contacts 212 correspondingly. The image sensor 22 may be a Complementary Metal Oxide Semiconductor (CMOS) image sensor or another appropriate image sensor. In one embodiment, the image sensor 22 may be integrated with an imaging lens to reduce the size of the image sensor 22.

The plurality of light-emitting elements 23 is disposed on the substrate 21, adjacent to the image sensor 22 and electrically connected with the plurality of corresponding third conductive contacts 213. In one embodiment, the plurality of light-emitting elements 23 respectively emits lights of different wavelengths and may be operated separately or simultaneously for observing different targets. It is easily understood: the lights generated by the plurality of light-emitting elements 23 may have the same wavelength for illumination or another application. For example, the light-emitting elements 23 may be white light-emitting diodes (LED), infrared LED, blue LED, ultraviolet LED, or a combination thereof.

The scattering layer 24 covers at least one sidewall of the light-emitting element 23. Refer to FIG. 2. In one embodiment, the scattering layer 24 is filled in the space between image sensor 22 and the light-emitting elements 23 and the space among the light-emitting elements 23. In one embodiment, the scattering layer 24 cooperates with the plurality of light-emitting elements 23 to form an annular structure surrounding the image sensor 22, as shown in FIG. 2. It is easily understood: the scattering layer 24 and the plurality of light-emitting elements 23 may cooperate to form an incomplete annular structure to meet practical requirement. For example, the scattering layer 24 and the plurality of light-emitting elements 23 may cooperate to form a strip-like structure surrounding the image sensor 22, such as a U-shaped structure, an L-shaped structure, or an I-shaped structure. In one embodiment, the scattering layer 24 includes a resin and microparticles dispersed in the resin. The microparticles in the resin may reflect or refract the lights generated by the light-emitting elements 23, whereby the light may be output from an upper surface 241 of the scattering layer 24. In one embodiment, the altitude of the upper surface 241 of the scattering layer 24 is lower than or equal to the altitude of a light-output surface 231 of the light-emitting element 23.

Based on the abovementioned structure, a light-input surface of the image sensor and a light-output surface of the light-emitting element are oriented toward the same direction. Therefore, the image sensor package of the present invention can increase the light utilization efficiency and provide more uniform illumination. Because the scattering layer 24 scatters the light generated by the light-emitting elements 23, the image sensor package of the present invention can provide an about-annular illumination light with further higher uniformity.

Refer to FIG. 3. In one embodiment, the light-emitting element 23 may include a secondary optical structure 25. The secondary optical structure 25 may adjust the light-output angle, whereby to increase the light utilization efficiency or increase the illumination distance. In one embodiment, the image sensor package 20 of the present invention further comprises a first encapsulant 26. The first encapsulant 26 encapsulates the sidewall of the image sensor 22 and a plurality of light-emitting elements 23. The first encapsulant 26 may be made of a high-transparency material, protecting the light-emitting elements 23 against collision by external objects and increasing humidity proof capability and ESD (electrostatic discharge) resistance of the light-emitting elements 23. In one embodiment, the altitude of a top surface of the first encapsulant 26 is equal to or lower than the altitude of a light-input surface 221 of the image sensor 22.

Refer to FIG. 3 again. In one embodiment, the image sensor package 20 of the present invention further comprises a conductive connection member 27 and a plurality of cables 273. The conductive connection member 27 includes a plurality of fourth conductive contacts 271 and a plurality of fifth conductive contacts 272, wherein the plurality of fourth conductive contacts 271 of the conductive connection member 27 is electrically connected with the plurality of corresponding first conductive contacts 211 of the substrate 21. In one embodiment, the conductive connection member 27 is a circuit board, such as a printed circuit board (PCB) or a flexible printed circuit (FPC). The plurality of cables 273 is electrically connected with the plurality of corresponding fifth conductive contacts 272. The plurality of cables 273 may function as power cords and signal transmission cables to enable the image sensor package 20 to electrically connect with external devices or systems, whereby the image sensor package 20 can receive power or transmit image signals to the rear-end controller or display device. In one embodiment, the image sensor package 20 of the present invention further comprises a second encapsulant 28. The second encapsulant 28 encapsulates the conductive connection member 27 and the ends of the plurality of cables 273 lest the cables 273 be detached from the conductive connection member 27.

It is easily understood: the relative altitude of the image sensor 22 and the light-emitting elements 23 may influence quality of illumination and images. For example, if the light-output surfaces 231 of the light-emitting elements 23 are too low with respect to the image sensor 22, the illumination light generated by the light-emitting elements 23 may be blocked by the image sensor 22, and shadows thus form. If the light-input surface 221 of the image sensor 22 is too low with respect to the light-emitting elements 23, the imaging light reflected from the inspected object may be blocked by the light-emitting elements 23, or the illumination light generated by the light-emitting elements 23 may directly project onto the light-input surface 221 of the image sensor 22. Both the cases would affect the imaging quality. Refer to FIG. 3 again. In one embodiment, the altitude of the light-output surfaces 231 of the light-emitting elements 23 are equal to or lower than the altitude of the light-input surface 221 of the image sensor 22 to optimize the quality of illumination and images. It is preferred: the difference of the altitude of the light-input surface 221 of the image sensor 22 and the altitude of the light-output surfaces 231 of the light-emitting elements 23 is smaller than or equal to 0.5 mm. In one embodiment, the substrate 21 includes a recess 214 or a drop, whereby the altitudes of the plurality of second conductive contacts 212 are equal to or lower than the altitudes of the plurality of third conductive contacts 213. Thus, after the image sensor 22 and the light-emitting elements 23 are disposed on the substrate 21 and respectively electrically connected with the corresponding second conductive contacts 212 and the corresponding third conductive contacts 213, the altitude of the light-input surface 221 of the image sensor 22 is equal to or higher than the altitude of the light-output surfaces 231 of the light-emitting elements 23.

Figure 4A:
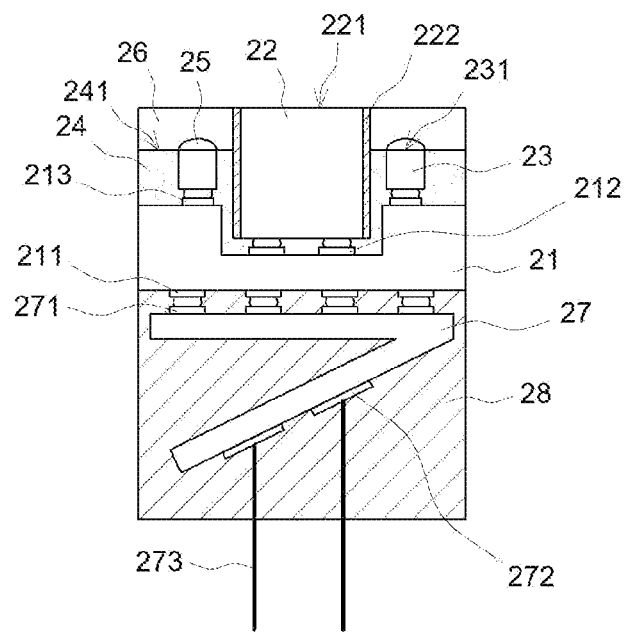
FIG. 4a is a diagram schematically showing an image sensor package according to a second embodiment of the present invention.
Figure 4B:
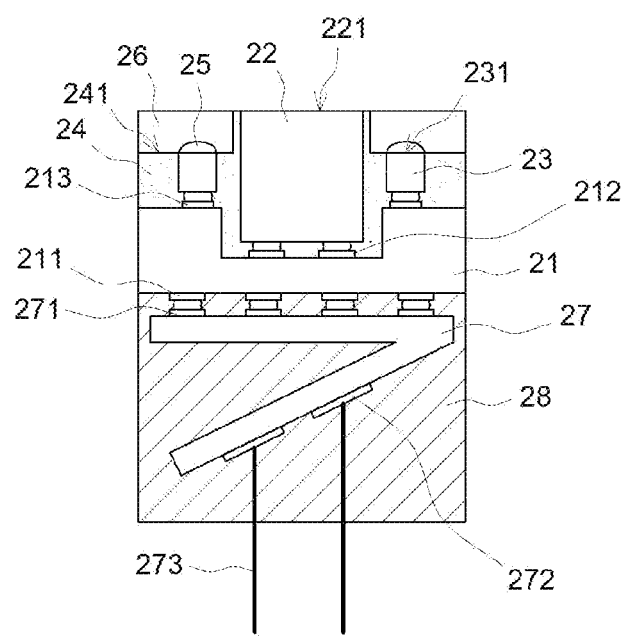
FIG. 4b is a diagram schematically showing an image sensor package according to a third embodiment of the present invention.

Besides, the illumination light generated by the light-emitting elements 23 may directly enter the imaging system of the image sensor 22 and affect the imaging quality. For example, the illumination light generated by the light-emitting elements 23 may enter into the region between the sensor and the imaging lens through the sidewall of the image sensor 22, whitening the images and degrading the imaging quality. Refer to FIG. 4a. In one embodiment, the image sensor 22 includes a light-shielding layer 222, which is arranged between image sensor 22 and the light-emitting elements 23. For example, the light-shielding layer 222 is disposed on the sidewall of the image sensor 22. The light-shielding layer 222 can prevent the illumination light generated by the light-emitting elements 23 from directly entering the imaging system of the image sensor 22 lest the imaging quality be affected. It is easily understood: as the microparticles of the scattering layer 24 can reflect or refract the light generated by the light-emitting elements 23 and decrease the light-permeability of the scattering layer 24, the scattering layer 24 also has the effect of decreasing the amount of the illumination light, which is generated by the light-emitting elements 23, passes through the sidewall of the image sensor 22 and enters into the image sensor 22. In other words, the scattering layer 24 also functions similarly to the light-shielding layer 222. Refer to FIG. 4b. In one embodiment, the scattering layer 24 is extended along the sidewall of the image sensor 22 to cover the sidewall of the image sensor 22, whereby is decreased in the amount of the illumination light, which is emitted by the light-emitting elements 23 and enters the image sensor 22 through the sidewall of the image sensor 22. It is easily understood: the present invention may have an embodiment wherein the image sensor 22 includes a light-shielding layer 222 and wherein the sidewall of the image sensor 22 is also covered by the scattering layer 24.

Figure 5:
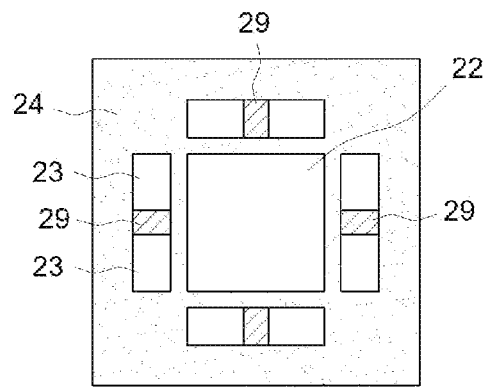
FIG. 5 is a diagram schematically showing an image sensor package according to a fourth embodiment of the present invention.
Figure 6:
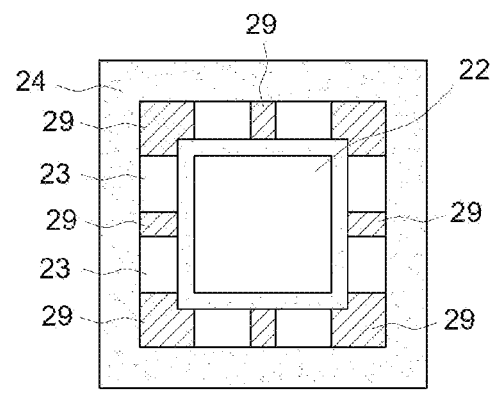
FIG. 6 is a diagram schematically showing an image sensor package according to a fifth embodiment of the present invention.

Refer to FIG. 5 and FIG. 6. In one embodiment, the image sensor package of the present invention further comprises a light-conduction layer 29. The light-conduction layer 29 is disposed among the plurality of light-emitting elements 23; the scattering layer 24 covers the sidewall of the light-conduction layer 29. The illumination light, which is emitted by the light-emitting elements 23, may enter the light-conduction layer 29; a portion of the illumination light may exit from the top surfaces of the light-conduction layer 29; a portion of the illumination light may enters the scattering layer 24, reflected or refracted by the scattering layer 24 and then exiting from the top surface of the scattering layer 24. Based on the abovementioned structure, the light-conduction layer 29 may cooperate with the plurality of light-emitting elements 23 to form an annular structure for providing annular illumination, as shown in FIG. 6. Alternatively, in one embodiment, the light-conduction layer 29 may cooperate with the plurality of light-emitting elements 23 to form strip-like structures for providing more uniform illumination and increasing the utilization efficiency of the illumination light, as shown in FIG. 5.

Figure 7:
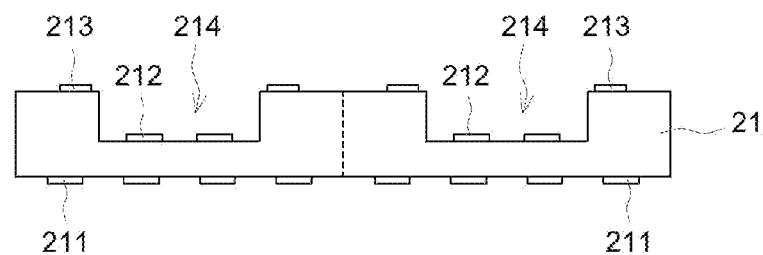
FIGS. 7-12 are diagrams schematically showing a method of fabricating the image sensor package according to the first embodiment of the present invention.

Refer to FIGS. 7-12 for the description of the method of fabricating the image sensor package 20 according to one embodiment of the present invention. Refer to FIG. 7. Firstly, provide a substrate 21, which includes a plurality of recesses 214 arranged in array, a plurality of first conductive contacts 211, a plurality of second conductive contacts 212, and a plurality of third conductive contacts 213, wherein the plurality of second conductive contacts 212 and the plurality of third conductive contacts 213 are electrically connected with the plurality of corresponding first conductive contacts 211 through the metal wires or another appropriate conduction circuit of the substrate 21.

Figure 8:
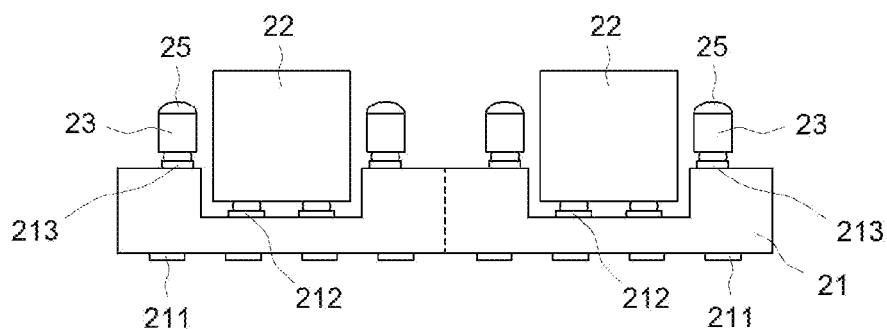

Refer to FIG. 8. Next, arrange the image sensors 22 and a plurality of light-emitting elements 23 on the substrate 21, wherein the image sensors 22 are disposed inside the recesses 214 for die bonding and electrically connected with the second conductive contacts 212 inside the recesses 214; the plurality of light-emitting elements 23 is electrically connected with the corresponding third conductive contacts 213. It should be noted: the sequence of bonding the image sensors 22 and the light-emitting elements 23 may be adjusted according to the requirement of the practical fabrication process. In one embodiment, a secondary optical structure 25 is disposed on the light-output surface of each light-emitting element 23.

Figure 9:
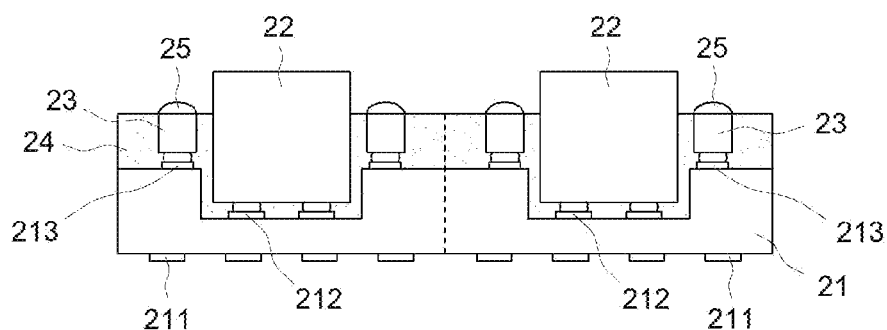

Refer to FIG. 9. Next, fill the resin containing microparticles to cover the sidewalls of the light-emitting elements 23; the resin is cured with ultraviolet light, heat or another appropriate method to form the scattering layer 24. In the embodiment shown in FIG. 9, the scattering layer 24 is filled into the space between the image sensor 22 and the light-emitting elements 23 and the space among the light-emitting elements 23. It is easily understood: the resin may be filled into the recesses 214 of the substrate 21 according to appropriate fabrication parameters.

Figure 10:
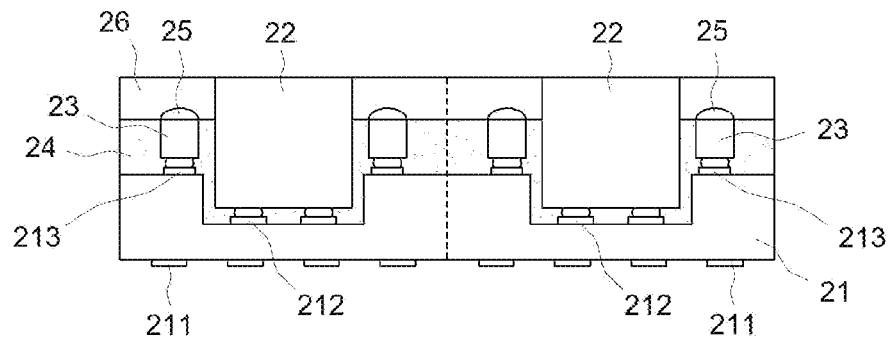

Refer to FIG. 10. Next, fill the first encapsulant 26 to encapsulate the sidewalls of the image sensors 22 and the sidewalls of the plurality of light-emitting elements 23; the first encapsulant 26 is cured with ultraviolet light, heat or another appropriate method. In one embodiment, the substrate 21 includes blocking walls surrounding the third conductive contacts 213, whereby to limit the space of filling the resin and the first encapsulant 26.

Figure 11:
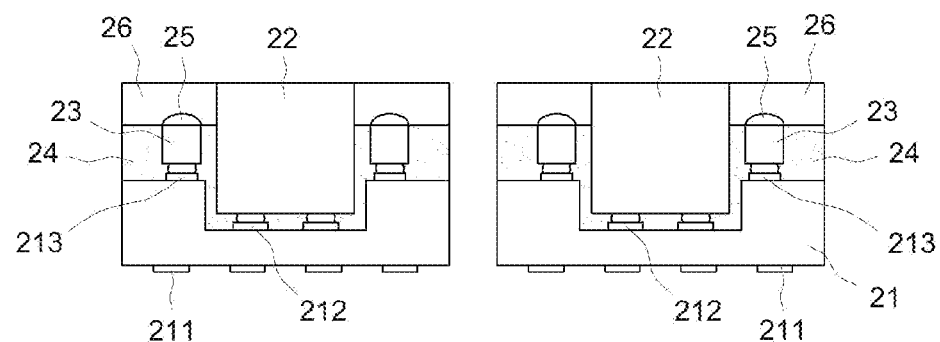

Next, cut the substrate 21 along the cutting alignment marks or the cutting lines, such as the dotted lines shown in FIG. 10, to form the image sensor modules each including the image sensor 22 and the plurality of light-emitting elements, as shown in FIG. 11. It is easily understood: the blocking walls of the substrate 21 may be removed simultaneously during the cutting process.

Figure 12:
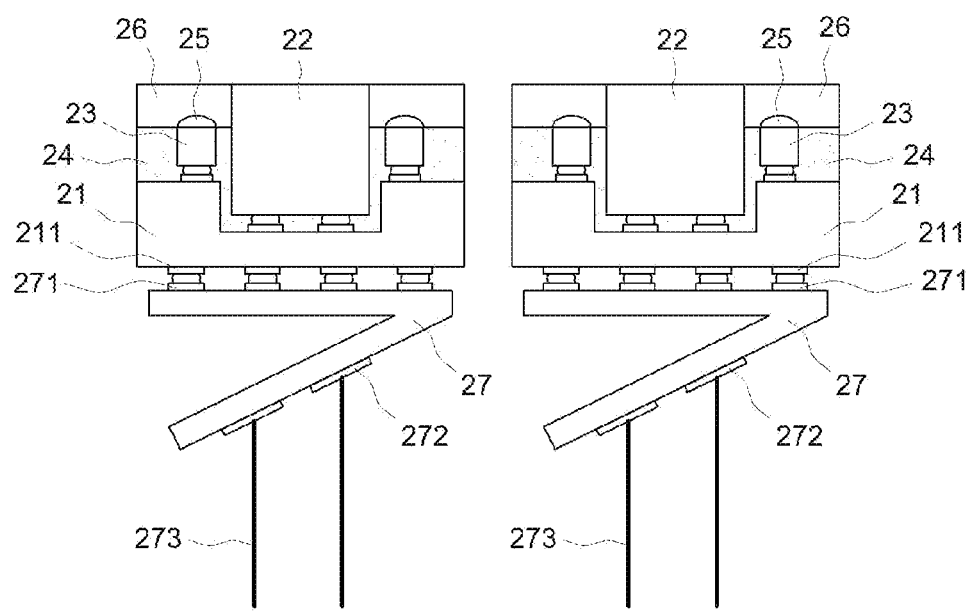

Refer to FIG. 12. Next, install the separated image sensor module on the conductive connection member 27 in the surface mount technology (SMT) or another appropriate technology, and then electrically connect the image sensor module with the conductive connection member 27. Next, electrically connect the plurality of cables 273 with the corresponding fifth conductive contacts 272 of the conductive connection member 27. Next, fill the second encapsulant 28 into the mold to make the second encapsulant 28 encapsulate the conductive connection member 27 and one end of each cables 273 to form the image sensor package 20 shown in FIG. 3.

Figure 13:
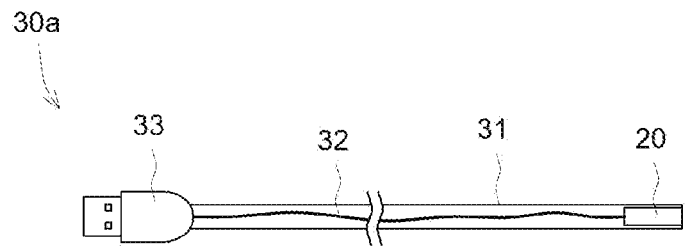
FIG. 13 is a diagram schematically showing an endoscope according to one embodiment of the present invention.

Refer to FIG. 13. In one embodiment, the endoscope 30a of the present invention comprises a tube 31, an image sensor package 20, a plurality of cables 32, and an electric connector 33. The tube 31 includes a first opening and a second opening. The end of the first opening of the tube 31 of the endoscope 30a is extended to a cavity, such as a cavity of a human body or a small space to be inspected in an industrial inspection. It is easily understood: the tube 31 may be designed to have different appearances to meet different applications. The image sensor package 20 is disposed at the first opening of the tube 31, whereby to capture images of a cavity and generate corresponding electronic signals. The detailed structure of the image sensor package 20 has been described hereinbefore and will not repeat again.

The cables 32 are respectively electrically connected with the image sensor package 20 and the electric connector 33, whereby the electronic signals generated by the image sensor package 20 may be transmitted to an external electronic device, such as a computer, a mobile Internet-access device or a dedicated electronic device of the endoscope, through the electric connector 33. In one embodiment, the electric connector 33 is electrically connected with an external electronic device in a pluggable way. The electric connector 33 may be a USB interface, a connection interface of a mobile Internet-access device, or another appropriate electric connector.

Figure 14:
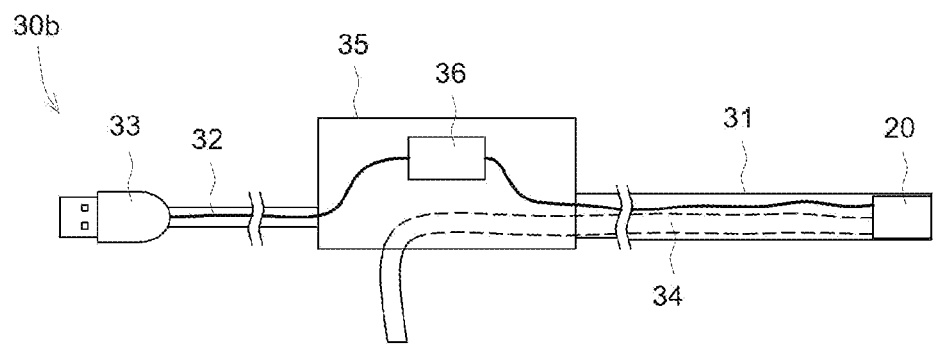
FIG. 14 is a diagram schematically showing an endoscope according to another embodiment of the present invention.

Refer to FIG. 14. In one embodiment, the tube 31 of the endoscope 30b of the present invention further includes a working channel 34. The operator may extend a working instrument through the working channel 34 into a cavity to undertake an intended work, such as sampling tissue, sucking out secretions/tissue fluids/blood, or supplying medicine.

In one embodiment, the endoscope 30b of the present invention further comprises a housing 35. The housing 35 is disposed between the tube 31 and the electric connector 33. The design of the housing 35 may be varied according to requirement. For an example, the housing 35 may have an appearance suitable to be held by the operator. For another example, the shape of the housing 35 is suitable to be mounted on a carrier, such as a carrier for a head-mounted device. In one embodiment, the endoscope 30b of the present invention further comprises an electronic element 36. The electronic element 36 is electrically connected with the image sensor package 20 and the electric connector 33. The electronic element 36 can process the electronic signals generated by the image sensor package 20 and transmit the electronic signals to an external electronic device through the electric connector 33. In one embodiment, the electronic element 36 is a microcontroller unit (MCU).

In conclusion, the present invention provides an image sensor package and an endoscope using the same, wherein a scattering layer covers the light-emitting elements and scatters the illumination light generated by the light-emitting elements to form a larger illumination light source, such as an annular, U-shaped, L-shaped or I-shaped illumination light source, whereby to achieve better illumination effect and increase the light utilization efficiency.

While the invention is susceptible to various modifications and alternative forms, a specific example thereof has been shown in the drawings and is herein described in detail. It should be understood, however, that the invention is not to be limited to the particular form disclosed, but to the contrary, the invention is to cover all modifications, equivalents, and alternatives falling within the appended claims.

What is claimed is:

1. An image sensor package, comprising
    a substrate comprising a plurality of first conductive contacts, a plurality of second conductive contacts, and a plurality of third conductive contacts, wherein the plurality of second conductive contacts and the plurality of third conductive contacts are electrically connected with the plurality of corresponding first conductive contacts;
    an image sensor, disposed on the substrate and electrically connected with the plurality of second conductive contacts;
    a plurality of light-emitting elements, disposed on the substrate, adjacent to the image sensor and electrically connected with the plurality of third conductive contacts;
    a scattering layer, covering at least one sidewall of the plurality of light-emitting elements and fill in the space between image sensor and light-emitting elements, an altitude of the scattering layer is lower than or equal to an altitude of a light-output surface of the plurality of light-emitting elements; and
    a first encapsulant, covering at the scattering layer and light-output surfaces of plurality of light-emitting element and encapsulating partial top sidewalls of the image sensor and the plurality of light-emitting elements,
    wherein an altitude of a top surface of the first encapsulant is equal to or lower than an altitude of a light-input surface of the image sensor.

2. The image sensor package according to claim 1, wherein the scattering layer is filled in space between image sensor and the plurality of light-emitting elements and space among the plurality of light-emitting elements.

3. The image sensor package according to claim 1, wherein the scattering layer and the plurality of light-emitting elements form a strip-like structure or an annular structure, which surrounds the image sensor.

4. The image sensor package according to claim 1, further comprising a light-conduction layer, disposed among the plurality of light-emitting elements, wherein the scattering layer covers a sidewall of the light-conduction layer.

5. The image sensor package according to claim 4, wherein the light-conduction layer and the plurality of light-emitting elements form a strip-like structure or an annular structure, which surrounds the image sensor.

6. The image sensor package according to claim 1, wherein the scattering layer includes a resin and microparticles dispersed in the resin.

7. The image sensor package according to claim 1, wherein the image sensor includes a light-shielding layer, which is disposed on a sidewall of the image sensor.

8. The image sensor package according to claim 1, wherein a portion of the scattering layer is extended along a sidewall of the image sensor to cover the sidewall of the image sensor.

9. The image sensor package according to claim 1, wherein altitudes of the plurality of second conductive contacts are equal to or lower than altitudes of the plurality of third conductive contacts.

10. The image sensor package according to claim 1, wherein an altitude of a light-output surface of the plurality of light-emitting elements is equal to or lower than an altitude of the light-input surface of the image sensor.

11. The image sensor package according to claim 1, wherein the plurality of light-emitting elements comprise a secondary optical structure.

12. The image sensor package according to claim 1, further comprising
a conductive connection member, including a plurality of fourth conductive contacts and a plurality of fifth conductive contacts, wherein the plurality of fourth conductive contacts is electrically connected with the plurality of corresponding first conductive contacts of the substrate; and
a plurality of cables, electrically connected with the plurality of corresponding fifth conductive contacts.

13. The image sensor package according to claim 12, further comprising
a second encapsulant, encapsulating the conductive connection member and one end of the plurality of wires.

14. An endoscope, comprising
a tube comprising a first opening and a second opening;
an image sensor package, disposed at the first opening of the tube to capture images and generate a corresponding electronic signal, and comprising:
  a substrate comprising a plurality of first conductive contacts, a plurality of second conductive contacts, and a plurality of third conductive contacts, wherein the plurality of second conductive contacts and the plurality of third conductive contacts are electrically connected with the plurality of corresponding first conductive contacts;
  an image sensor, disposed on the substrate and electrically connected with the plurality of second conductive contacts;
  a plurality of light-emitting elements, disposed on the substrate, adjacent to the image sensor and electrically connected with the plurality of third conductive contacts;
  a scattering layer, covering at least one sidewall of the plurality of light-emitting elements and fill in the space between image sensor and light-emitting elements, an altitude of the scattering layer is lower than or equal to an altitude of a light-output surface of the plurality of light-emitting elements; and
  a first encapsulant, covering at the scattering layer and light-output surfaces of a plurality of light-emitting elements and encapsulating partial top sidewalls of the image sensor and the plurality of light-emitting elements, wherein an altitude of a top surface of the first encapsulant is equal to or lower than an altitude of a light-input surface of the image sensor;
a plurality of cables, disposed inside the tube, wherein one end of the plurality of cables is electrically connected with the plurality of corresponding first conductive contacts of the substrate; and
an electric connector, electrically connected with another end of the plurality of cables.

15. The endoscope according to claim 14, further comprising
an electronic element, electrically connected with the image sensor package and the electric connector, and processing the electronic signals generated by the image sensor package.

16. The endoscope according to claim 14, further comprising
a housing, disposed between the image sensor package and the electric connector.

17. The endoscope according to claim 14, wherein the scattering layer is filled in space between image sensor and the plurality of light-emitting elements and space among the plurality of light-emitting elements.

18. The endoscope according to claim 14, wherein the scattering layer and the plurality of light-emitting elements form an annular structure, which surrounds the image sensor.

19. The endoscope according to claim 14, further comprising
a light-conduction layer, disposed among the plurality of light-emitting elements, wherein the scattering layer covers a sidewall of the light-conduction layer.

20. The endoscope according to claim 19, wherein the light-conduction layer and the plurality of light-emitting elements form an annular structure, which surrounds the image sensor.

21. The endoscope according to claim 14, wherein the scattering layer includes a resin and microparticles dispersed in the resin.

22. The endoscope according to claim 14, wherein the image sensor includes a light-shielding layer, which is disposed on a sidewall of the image sensor.

23. The endoscope according to claim 14, wherein a portion of the scattering layer is extended along a sidewall of the image sensor to cover the sidewall of the image sensor.

24. The endoscope according to claim 14, wherein altitudes of the plurality of second conductive contacts are equal to or lower than altitudes of the plurality of third conductive contacts.

25. The endoscope according to claim 14, wherein an altitude of a light-output surface of the plurality of light-emitting elements is equal to or lower than an altitude of a light-input surface of the image sensor.

26. The endoscope according to claim 14, wherein the plurality of light-emitting elements comprise a secondary optical structure.

27. The endoscope according to claim 14, wherein the image sensor package further comprises
a conductive connection member, including a plurality of fourth conductive contacts and a plurality of fifth conductive contacts, wherein the plurality of fourth conductive contacts is electrically connected with the plurality of corresponding first conductive contacts of the substrate; and a plurality of wires, electrically connected with the plurality of corresponding fifth conductive contacts.

28. The endoscope according to claim 27, wherein the image sensor package further comprises a second encapsulant, encapsulating the conductive connection member and one end of the plurality of wires.

* * * * *